Figure 1:
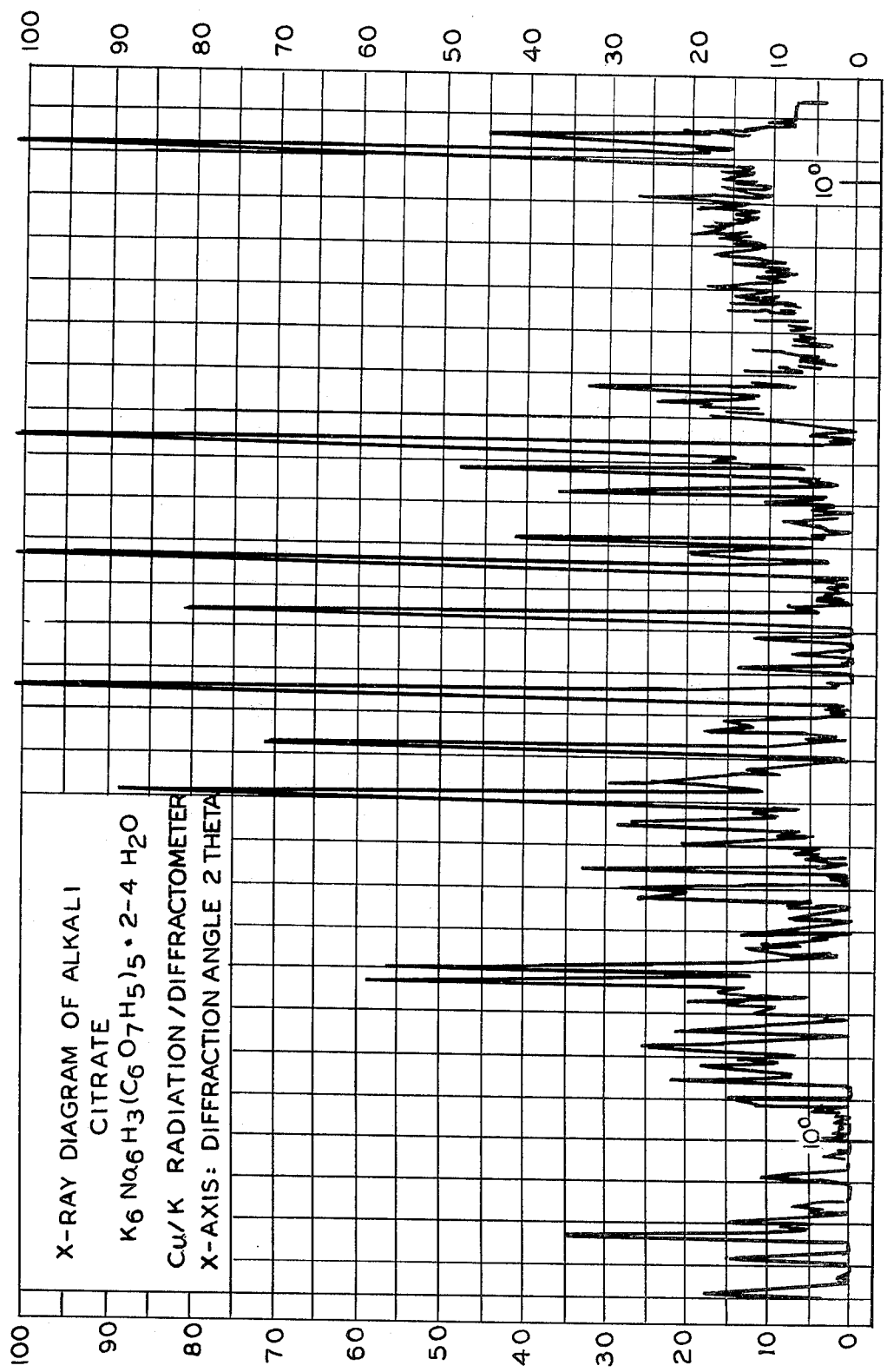

United States Patent [19]

Madaus et al.

[11] 4,400,535

[45] Aug. 23, 1983

[54] ACIDIC ALKALI CITRATE AND COMPOSITIONS FOR ADJUSTING THE PH OF URINE

[75] Inventors: Rolf Madaus, Köln-Brück; Werner Stumpf; Klaus Görler, both of Bensberg-Refrath, all of Fed. Rep. of Germany; Alfonso Carcasona-Beltrán, Barcelona, Spain

[73] Assignee: Dr. Madaus & Co., Ostmerheimer, Fed. Rep. of Germany

[21] Appl. No.: 223,646

[22] Filed: Jan. 9, 1981

Related U.S. Application Data

[63] Continuation of Ser. No. 112,994, Jan. 17, 1980, abandoned, which is a continuation of Ser. No. 916,373, Jun. 16, 1978, abandoned.

[51] Int. Cl.$^3$ .................... C07C 51/43; C07C 59/265; A61K 31/19
[52] U.S. Cl. .................................... 562/584; 424/317
[58] Field of Search ..................... 562/584; 424/317

[56] References Cited

U.S. PATENT DOCUMENTS

| Re. 28,192 | 10/1974 | Schulz | 562/584 |
| 2,159,155 | 5/1939 | Holten | 562/584 |
| 2,904,573 | 9/1959 | Oroshnik et al. | 424/317 |
| 3,658,969 | 4/1972 | Vaille | 424/317 |
| 3,819,696 | 6/1974 | Kominek | 562/584 |

OTHER PUBLICATIONS

Kirk–Othmer "Encyclopedia of Chemical Technology", 2nd Ed., (1965), vol. 5, pp. 530 & 539.

*Primary Examiner*—Natalie Trousof
*Assistant Examiner*—L. Hendriksen
*Attorney, Agent, or Firm*—Felfe & Lynch

[57] ABSTRACT

The invention provides a novel acidic alkali citrate having the formula $K_6Na_6H_3(C_6O_7H_5)_5.2$–$4\ H_2O$ made by dissolving either (a) trisodium citrate $\times 2\ H_2O$, tripotassium citrate $\times 1\ H_2O$, and citric acid in a mole ratio of 2:2:1 in 3 to 5 times the quantity by weight of boiling demineralized water, based on the weight of the citric acid and maintaining the solution at a temperature not lower than 60° C.; or (b) citric acid at 90° C. while stirring in 0.1 to 1 times its weight of demineralized water and then adding sodium carbonate and potassium carbonate to give a mole ratio of 3:3:5 of sodium carbonate:potassium carbonate:citric acid, and quick drying the homogeneous solution obtained. Therapeutic agents for the treatment of urolithiasis and removal, or preventing recurrence, of urine stones comprising said acidic alkali citrate are provided.

4 Claims, 2 Drawing Figures

ACIDIC ALKALI CITRATE AND COMPOSITIONS FOR ADJUSTING THE PH OF URINE

This is a continuation of application Ser. No. 112,994, filed Jan. 17, 1980 (now abandoned), which is a continuation of Ser. No. 916,373, filed June 16, 1978, now abandoned.

The invention relates to an acidic alkali citrate of the formula $K_6Na_6H_3(C_6O_7H_5)_5.2-4\ H_2O$, its preparation process and medications containing same.

Uric acid develops in the human organism as a final product of the purine metabolism. Dependent on the pH-value of the urine, a displacement of the highly soluble urate salts may occur in favor of the less soluble salts or undissociated uric acid. The solubility increases again at pH-values of more than 6 and at physiological concentrations, and precipitated uric acid already tends to enter again into solution. For the treatment of patients suffering from uroliths, agents which increase the uric pH-value are therefore administered. The classic method of such a treatment is the administration of lemons (B. Bibus, Wicn, Med. Wschr. 118, 416 (1968)). This method, has, however, the disadvantage of potentially inaccurate doing as well as gastric incompatibility. A controlled increase of the uric pH-value was sought to be reached years ago by administration of an alkali-citric acid-mixture in a syrup-like solution (H. Eisenburg et al, J. Clin. Endocrin. 15, 503 (1955)), or also of dry mixtures of sodium citrate, potassium citrate and citric acid (Der Urologe, 4, 156, (1965)).

The syrup-like solution must, however, be freshly prepared before use. Moreover, it contains sugar (diabetes-contra-indication). The hitherto mentioned proposed dry mixtures now led in the course of time to a lumpy mixture caused by topochemical reactions and were thus also not satisfactory. It has also been proposed to use dry preparations containing citrate in granulated form or as tablets containing ion sources other than citrate. These preparations, too, however, were found not to be stable.

Therefore, there has been a need for a stable and storable product to produce a pH-value in urine of between 612 and 7.0 after setting free the citrate-, sodium-, and potassium ions in an exactly defined proportion corresponding to the predetermined dosage. pH-values below 6.2 are insufficient for lithotriptic treatment; values higher than 7.0 pose the danger of phosphate-coat formation around the urolith, preventing the dissolution of the stone. The above pH-values must therefore be adhered to exactly for successful therapy.

It is therefore the objective of the invention to provide a solid product which is stable and indefinitely storable and which releases citrate-, sodium-, and potassium ions in certain equivalent proportions when used as a therapeutic agent, producing, at the proper dosage, a therapeutically desired pH increase of the urine to pH 6.2–7.0. The product of the invention has a good compatibility, allows simple dosing, and dissolves uroliths as well as preventing their recurrence.

Surprisingly, it has been found when producing a concentrated aqueous alkaline hydrogen citrate solution that anomalies arise which are thought to be due to complex formation by these salts in solutions: derivatives are observed between the calculated values and the experimentally obtained values of the mobility and activity of the sodium ions, when determining their electrochemical potentials. When measuring nuclear spin resonance, results pointing also to complex formation in sodium-citrate solutions are obtained. Surprisingly, it has furthermore been found that stable, homogeneous and storable products can be obtained by suddenly cooling high ion concentration solutions; these products have desirable uric pH-value influencing properties and activites. The individual components for making the inventive agents, viz., sodium carbonate, potassium carbonate and/or sodium hydroxide, or potassium hydroxide and citric acid, react in a mole ratio of 3:3:5 in the case of carbonates and 6:6:5 in the case of hydroxides, in aqueous solution. The reaction may preferably also take place in solutions of trisodium citrate×2 $H_2O$, tripotassium citrate×1 $H_2O$, and citric acid in a mole ratio of 2:2:1. These initial components are surprisingly not detectable in the final product. The obtained acidic alkali citrate rather exists in the condition of a defined crystalline product. Administration of the product according to the invention to patients with hyperuricuria (increase of uric acid in the urine) permits facile control of the dosage and, thus, effects an exact therapeutic pH-increase of the urine. The uroliths are dissolved and their re-formation is prevented. The product has the formula $K_6Na_6H_3(C_6O_7H_5)_5.2-4\ H_2O$. Since the inventive agent is free of carbohydrates it has special advantages for diabetics who represent a large part of uric acid patients. The pH-regulating effect is reached with comparatively low dosages, for example, 10 g/day. A medication over a period of years is possible because of the good compatibility of the compound.

A further aspect of the invention is a process for obtaining the acidic alkali citrate of the formula $K_6Na_6H_3(C_6O_7H_5)_5.\ 2-4\ H_2O$. Essentially, the process of the invention comprises dissolving trisodium citrate×2 $H_2O$, tripotassium citrate×1 $H_2O$ and citric acid in a mole ratio of 2:2:1 in 3 to 5 times, especially 3.7 times, the quantity by weight of boiling water relative to the weight of citric acid dissolved. The temperature of the solution is not allowed to be below 60° C., and the homogeneous solution is subjected to quick drying.

The process can also be effected by dissolving citric acid in 0.5 to 1.0 times, especially 0.63 times, its quantity by weight of demineralized water relative to the weight of citric acid put in, at 90° C. while stirring, and then adding sodium carbonate and potassium carbonate in solid from at a mole ratio of citric acid:potassium carbonate:sodium carbonate of 5:3:3. The hot solution is then worked up as described above.

When using NaOH and KOH, or $NaHCO_3$ and $KHCO_3$, accordingly adjusted mole ratios have to be considered.

A reverse sequence of addition is possible, i.e., firstly adding alkali carbonate and then citric acid. The water hydration content is adjusted to be approximately 2–5%.

Pharmacological and clinical testing by the inventors of the agent according to the invention led to the following observations which indicate a certain mechanism of action: In body cells citric acid is oxidized to 6 $CO_2$ and B 6 $H_2O$. A person of 70 kg of weight can oxidatively convert approximately 200 mMoles of citrate per hour. Metabolically, 1 mole of the acid alkali citrate according to the invention gives 5 moles of citric acid which are quantitatively metabolized into $CO_2$ and $H_2O$. At the same time 12 mole of $OH^-$ ions are developed which are available for acid neutralization. For example:

$$K_6Na_6H_3(C_6O_7H_5)_5 \times 3\ H_2O + 3\ H_2O = 5\ (C_6O_7H_8) + 6\ K^+ + 6\ Na^+ + 12\ OH^-$$

This indicates that 2.5 g of the acidic alkali citrate according to the invention administered orally causes lowering, by 22 mMoles, of $H^+$ ion elimination. As the pH of urine is influenced by the phosphate buffer mixture, and the body eliminates approximately 30 mMoles of phosphate ions per day, 30 mMoles of $H^+$ ions are conserved when changing from $H_2PO_4^-$ to $HPO_4^{--}$. Thereby the pH-value would already be increased from 4.8 to approximately 6.5. If $HPO_4^{--}$ ions were changed still further, to $PO_4^{---}$, another 30 mMoles would be conserved, and the pH-value would be higher than 7.0. These values are registered by the titration acidity of the urine of approximately 30–50 mMoles a day. In order to reach an effective neutralization of the urine one must therefore employ at least 5.0 g of the acidic alkali citrate. But since from pH 6.0 on the tubules of the kidney react with an increased elimination of citrate and $CHO_3^-$ whereby the $H^+$ ions are bound, and the secretion of $NH_4^+$ ions is decreased by approximately 30–50 mMoles, in fact double that dosage is necessary. Thus, about 10 g of the inventive acidic alkali citrate corresponds to the usual dosage in practice. The necessary dosage may be lower as $PO_4^{---}$ elimination decreases and raised when the $PO_4^{---}$ elimination is greater. By adding the mMoles of titration acidity (A) and mMoles of $NH_4^+$ in urine over 24 hours, the necessary dosage of alkali citrate can individually be prescribed. For the inventive acidic alkali citrate the following formula can be used:

$$\frac{\text{mMole}\ A/24\ \text{hours} + \text{mMole}\ NH_4^+/24\ \text{hours}}{9} = \text{g compound/day}$$

(wherein "compound" is the inventive acidic alkali citrate). In the use of the new compound against uroliths and in uric acid diathesis the urine pH-value of the patients is controlled. To simplify matters, the patient can do this himself using indicator paper and keeping a control calendar. The compound is dosed to produce the desired effect, i.e., the pH-value must be determined before each administration and the dosage determined therefrom. The average daily dosage is 10 g and should be ingested, preferably together with a liquid, gradually during the day. Preferred are 2.5 g in the morning, 2.5 g at noon, and 5.0 g in the evening. In any case the individual dosage is to be determined to bring the pH-value of urine into the optimal range of between 6.2 and 7.0.

The following conditions are determining factors for the diagnosis: typical complaints (colics) and haematuria, proof of uric acid crystals in the sediment (brick dust deposit), analysis of the passed concrement, constant urine pH-values below 5.5, uric acid in serum of more than 5.5 mg/100 ml in men and more than 4.3 mg/100 ml in women, indication of the existence of stones by X-rays, by brightening or recess in the excretion urogram or a retrograde pyelogram. The inventive acidic alkali citrate $K_6Na_6H_3(C_6O_7H_5)_5 \times 2$–$4\ H_2O$ should be the therapy of choice for uroliths, uric acid diathesis, and general stone formation proclivity. Past clinical tests show a success rate of 95%. The treatment is not effective in only very few special cases. These are mostly strong shade throwing concrements (mixed stones) and uncontrolled infections of the urinary passages. The only danger in administration of the inventive agent is a hyperalkalinity due to wrong and excessive dosing over a long time leading to exceeding the upper limit of the pH-value of 7.0; as a result of this, phosphate stones may develop. When adjusting the urinary pH-values to 6.2 to 7.0 the following clinical results were found:
(1) disappearance of the subjective complaints (feeling of pressure and tension in the renal region, typical colics),
(2) inhibited microhaematuria,
(3) brick dust deposit no longer demonstrable
(4) X-ray control shows a diminution or a break-up of the concrement.

The necessary duration of the treatment depends on the position, form, size and age of the stone. The lithotriptic effect is obviously better, the greater the quantity of urine which surrounds the stone.

EXAMPLE 1

194.4 kg of tripotassium citrate×1 $H_2O$, 176.4 kg trisodium citrate×2 $H_2O$, and 57.6 kg citric acid are dissolved in 210.0 l of boiling demineralized water. The temperature of the solution is then slowly lowered to about 70°–80° C., taking care that no particles precipitate. Thereafter the homogeneous solution is transferred continuously onto a two-roller-drier by means of a pump and rapidly dried. The layer thickness on the rollers is 0.5 to 0.8 mm. The dry rollers are acted upon on the inside with saturated steam of 5–7 excess atmosphere of pressure so that a temperature of 140°–160° C. of the roller suface results. By adjusting the rotation speed, the product is made to stay on the roller for about 5 seconds. The output is 30–35 kg of dry product per $m^2$ heating surface and hour. The cylinders of the rollers are of fine grained special gray cast iron with perlitic constitution, turned outside and inside, ground and strongly hard-chrome plated. The residual final drying is effected on plate driers to about 3% $H_2O$.

Figure 2:
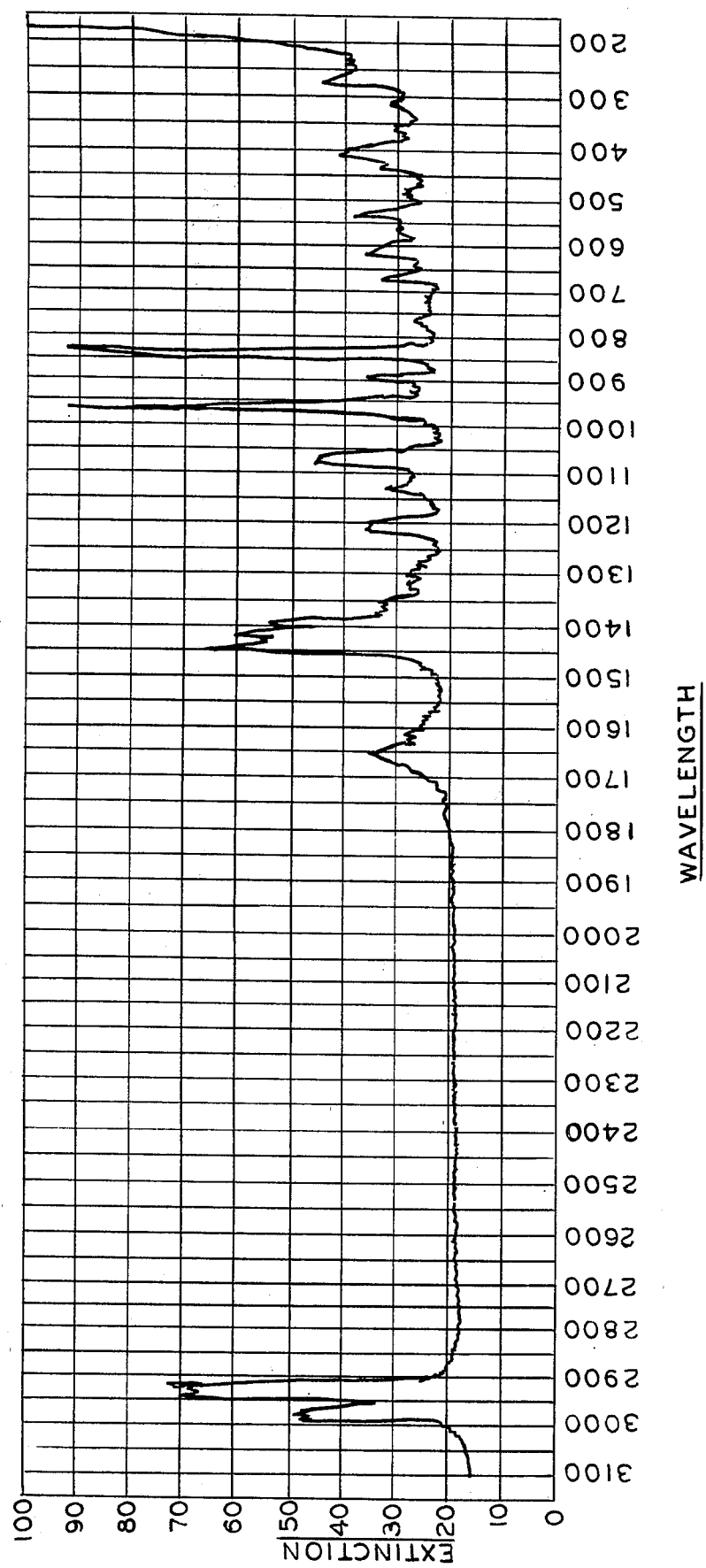

X-ray diagram
(goniometric picture of the X-ray diffraction spectrum (see FIG. 1)
Raman spectrum (see FIG. 2)

| Analytical composition | found | theoretical |
|---|---|---|
| Potassium | 17.40% | 17.76% |
| Sodium | 10.42% | 10.44% |
| Citrate (total) | 71.77% | 71.57% |
| (all values refer to the anhydrous substance) | | |

EXAMPLE 2

1,050.50 kg of citric acid are suspended while stirring in 675 l of demineralized water at about 90° C. A part of the citric acid does not dissolve initially. Then 317.97 kg of sodium carbonate (anhydrous) in solid form and 414.63 kg of potassium carbonate (anhydrous) are added while stirring and maintaining the above temperature. On completion of the reaction no more $CO_2$ is evolved and all substances are in solution. The solution is worked up as in Example 1. The product obtained has the same elementary analysis and X-ray diffraction spectrum as that of Example 1.

EXAMPLE 3

317.97 kg of sodium carbonate (anhydrous) and 414.63 kg of potassium carbonate (anhydrous) are suspended while stirring in 675 l of water at 90° C. Then 1,050.50 kg of citric acid in solid form are slowly added, while keeping the above temperature and stirring, until the reaction is finished. No more $CO_2$ is separated. Thereafter the process is continued as described in Example 1.

We claim:

1. Process for preparing acidic citrate of the formula $$K_6Na_6H_3(C_6O_7H_5)_5 \cdot 2\text{--}4\ H_2O$$

comprising the steps of dissolving tripotassium citrate $\cdot H_2O$, trisodium citrate$\cdot 2\ H_2O$ and citric acid in a mole ratio 2:2:1 together in 3 to 5 times the quantity by weight of boiling demineralized water, based on the weight of the citric acid, while maintaining the temperature of the solution at not lower than 60° C., dissolving citric acid in 0.5 to 1 times its quantity by weight of demineralized water, based on the weight of the citric acid inserted, at 90° C., then adding sodium carbonate and potassium carbonate in solid form to give a mole ratio of 3:3:5 of sodium carbonate, potassium carbonate and citric acid; and quick drying the homogeneous solution by contact with a hot surface at 140° C. to 160° C. for about 5 seconds.

2. Process as claimed in claim 1 wherein said trisodium citrate$\cdot 2\ H_2O$, tripotassium citrate$\cdot 1\ H_2O$ and citric acid are dissolved in 3.7 times the quantity by weight of demineralized water, based on the weight of said citric acid.

3. Process as claimed in claim 1 wherein said citric acid, and then said sodium carbonate and potassium carbonate, are dissolved in 0.63 times the quantity by weight of demineralized water, based on the weight of said citric acid.

4. The process of claim 1 wherein said quick drying comprises
transferring said homogeneous solution into contact with dry heated rollers forming said heated surface.

* * * * *